United States Patent [19]

Kaeding

[11] Patent Number: 4,849,573
[45] Date of Patent: Jul. 18, 1989

[54] PROCESS FOR MANUFACTURING LIGHT OLEFINS

[75] Inventor: Warren W. Kaeding, Lawrenceville, N.J.

[73] Assignee: Mobil Oil Corporation, New York, N.Y.

[21] Appl. No.: 246,024

[22] Filed: Sep. 14, 1988

Related U.S. Application Data

[63] Continuation of Ser. No. 36,189, Apr. 9, 1987, abandoned, which is a continuation of Ser. No. 500,489, Jun. 2, 1983, abandoned, which is a continuation of Ser. No. 383,069, May 28, 1982, abandoned, which is a continuation of Ser. No. 939,596, Sep. 5, 1978, abandoned.

[51] Int. Cl.$^4$ ............................................. C07C 1/00
[52] U.S. Cl. ..................................... 585/640; 585/733
[58] Field of Search ........................................ 585/640

[56] References Cited

U.S. PATENT DOCUMENTS

| | | | |
|---|---|---|---|
| 4,025,575 | 5/1977 | Chang et al. | 585/640 |
| 4,083,888 | 4/1978 | Caeser et al. | 585/640 |
| 4,083,889 | 4/1978 | Caeser et al. | 585/640 |

FOREIGN PATENT DOCUMENTS 2615150 10/1976 Fed. Rep. of Germany.

Primary Examiner—Curtis R. Davis
Attorney, Agent, or Firm—Alexander J. McKillop; Charles J. Speciale; Edward F. Kenehan, Jr.

[57] ABSTRACT

Methanol is catalytically converted to hydrocarbons with high yield of light olefins. The catalysts employed are crystalline aluminosilicate zeolites having high silica to alumina ratios and the conversion is conducted at temperatures of from about 350° C. to 600° C. and at pressures ranging between about 1 atmospheres to about 100 atmospheres.

19 Claims, 2 Drawing Sheets

TABLE IV: C2-C4 OLEFIN/PARAFFIN RATIO

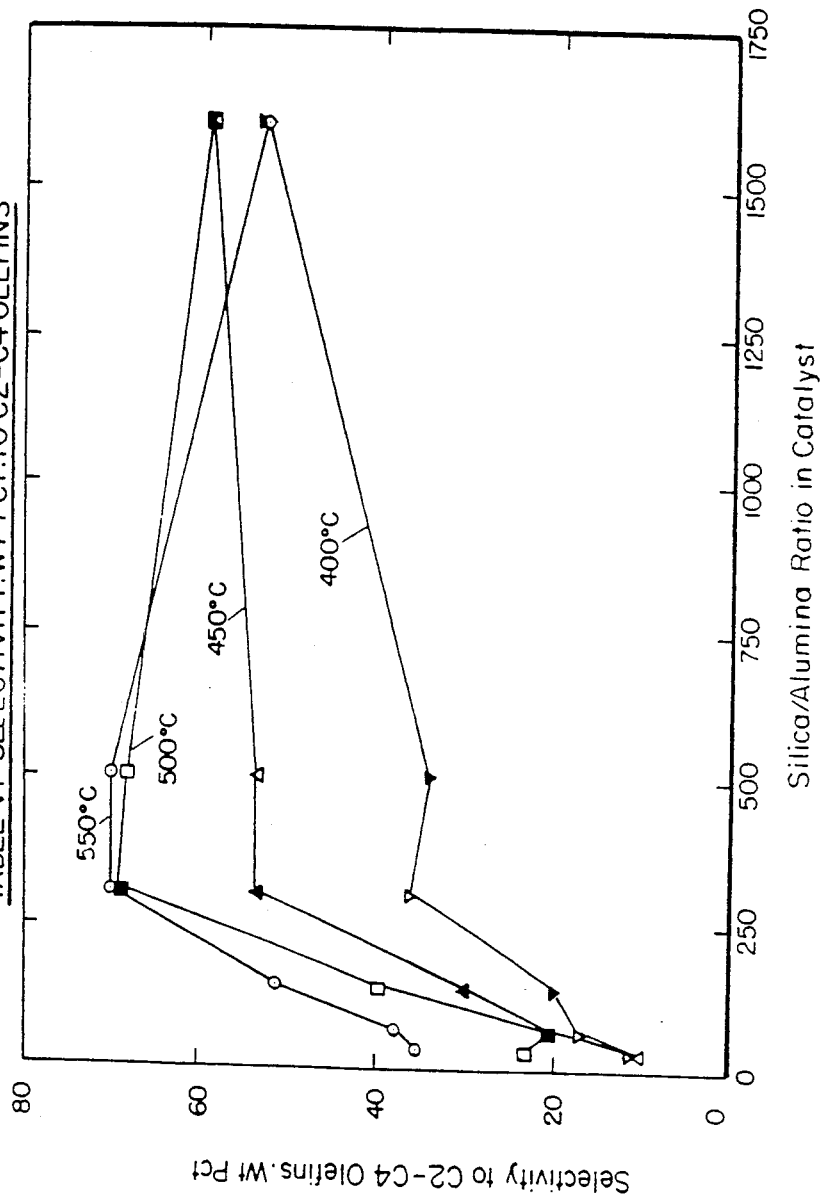

PROCESS FOR MANUFACTURING LIGHT OLEFINS

CROSS REFERENCE TO RELATED APPLICATIONS

This application is a continuation of copending U.S. application Ser. No. 036,189, filed Apr. 9, 1987, now abandoned. This Ser. No. 036,189 is a continuation of U.S. application Ser. No. 500,489, filed June 2, 1983, now abandoned. This Ser. No. 500,489 is a continuation of U.S. application Ser. No. 383,069, filed May 28, 1982, now abandoned. This Ser. No. 383,069 is a continuation of Ser. No. 939,596, filed Sept. 5, 1978, now abandoned.

BACKGROUND OF THE INVENTION

1. Field of the Invention

This invention is concerned with the manufacture of olefins. It is particularly concerned with the catalytic conversion of an alcohol feed to a hydrocarbon mixture having a high content of light olefins.

2. Description of the Prior Art

Zeolitic materials, both natural and synthetic, have been demonstrated in the past to have catalytic properties for various types of hydrocarbon conversions. One such conversion, which has generated considerable interest, is the manufacture of olefins from alcohols and ethers.

U.S. Pat. No. 4,025,575 describes a process by which lower alcohols and/or their ethers are converted to a mixture of $C_2$ to $C_5$ olefins by contact at subatmospheric inlet partial pressure with a crystalline aluminosilicate zeolite catalyst having a constraing index of 1 to 12 and a silica to alumina ratio of at least 12.

The production of olefins from aliphatic ethers by catalytic conversion with, for example, an HZSM-5 zeolite catalyst is described in U.S. Pat. No. 3,894,106 issued July 8, 1975.

The use of diluents to dissipate exothermic heat in a two stage conversion of methanol to gasoline is described in U.S. Pat. No. 3,931,349 issued Jan. 9, 1976.

A two-stage conversion of a lower alcohol to olefins or to gasoline, which employs a tubular reactor for the second stage, is described in U.S. Pat. No. 4,058,576.

A process for the manufacture of ethylene by catalytic conversion of methanol in the presence of a substantially anhydrous diluent and a zeolite catalyst such as HZSM-5 is described in U.S. Pat. No. 4,083,888 issued Apr. 11, 1978.

The effect of the rate of feedstock flow past the zeolitic catalyst in a continuous reaction mechanism involving the conversion of methanol to hydrocarbons has been studied and reported in the scientific literature (C. D. Chang and A. J. Silvestri, *Journal of Catalysis*, 47 249 (1977)). The results, which are summarized in TABLE I, show that at a liquid hourly space velocity (LHSV) of 1, the selectively ratio of $C_2$–$C_4$ olefins/paraffins is 2.8/41.1 or 0.068. By increasing the LHSV of the methanol feed to 108 and 1,080, however, this ratio changes to 5.28 and 4.95, respectively, indicating a preference for the formation of olefins over paraffins at higher space velocities. The overall conversion to hydrocarbons, however, is reduced significantly as the velocity is increased (100% at LHSV=1; 48% at LHSV=108; 9% at LHSV=1,080). Obviously, production costs would be significantly higher at the low conversion/high space velocity conditions than would the costs of a process where near 100% conversion of methanol to hydrocarbons could be realized.

TABLE I

EFFECT OF SPACE VELOCITY ON METHANOL CONVERSION AND HYDROCARBON DISTRIBUTION

| LHSV [vol of liquid methanol/ (vol of catalyst/hr)] | 1 | 108 | 1080 |
|---|---|---|---|
| Product distribution (wt %) | | | |
| Water | 56.0 | 33.0 | 8.9 |
| Methanol | 0.0 | 21.4 | 67.4 |
| Dimethyl ether | 0.0 | 31.0 | 23.5 |
| Hydrocarbons | 44.0 | 14.6 | 0.2 |
| Conversion (MeOH + MeOMe) (wt %) | 100.0 | 47.5 | 9.1 |
| Hydrocarbon distribution (wt %) | | | |
| Methane | 1.1 | 1.1 | 1.5 |
| Ethane | 0.6 | 0.1 | — |
| Ethylene | 0.5 | 12.4 | 18.1 |
| Propane | 16.2 | 2.5 | 2.0 |
| Propylene | 1.0 | 26.7 | 48.2 |
| i-Butane | 18.7 | 6.5 | 13.8 |
| n-Butane | 5.6 | 1.3 | — |
| Butenes | 1.3 | 15.8 | 11.9 |
| $C_3$ + Aliphatics | 14.0 | 27.0 | 4.4 |
| Aromatics | 41.1 | 6.6 | — |

Furthermore, the conversion of methanol to hydrocarbons is an exothermic reaction, evolving approximately 700 Btu of heat for each pound of reactant. Removal of such heat of reaction is a major problem, particularly in larger sized catalyst beds, and limits the methanol feed rate to low space velocities. Although high olefin/paraffin ratios can be obtained at high space velocities, heat removal and the need to separate, purify and recycle unreacted methanol at low conversions have made this route commercially impractical.

SUMMARY OF THE INVENTION

It has now been discovered that, in the catalytic conversion of alcohols to hydrocarbon compounds, the proportion of olefinic hydrocarbons in the product stream can be desirably and dramatically increased by contacting the vaporous alcohol with a zeolite catalyst having a high silica to alumina ratio. Of particular significance is the selective production of low molecular weight olefins (e.g. —$C_nH_{2n}$, where n=2–4), at high rates of conversion, from methanol feedstock.

The conversion is carried out by bringing the alcohol, such as methanol, into contact with a zeolite catalyst having a silica to alumina ratio of at least 140, and preferably greater than 298, under conditions of temperature and pressure conducive to conversion of the alcohol to hydrocarbons. The preferred reaction conditions include temperatures of between about 400° C. and 550° C. and pressures of from about 1 atmospheres to 100 atmospheres.

BRIEF DESCRIPTION OF THE DRAWINGS

FIG. I is a graphical illustration of the data of TABLE IV.

FIG. II is a graphical illustration of the data of TABLE V.

DESCRIPTION OF THE PREFERRED EMBODIMENTS

Figure 1:
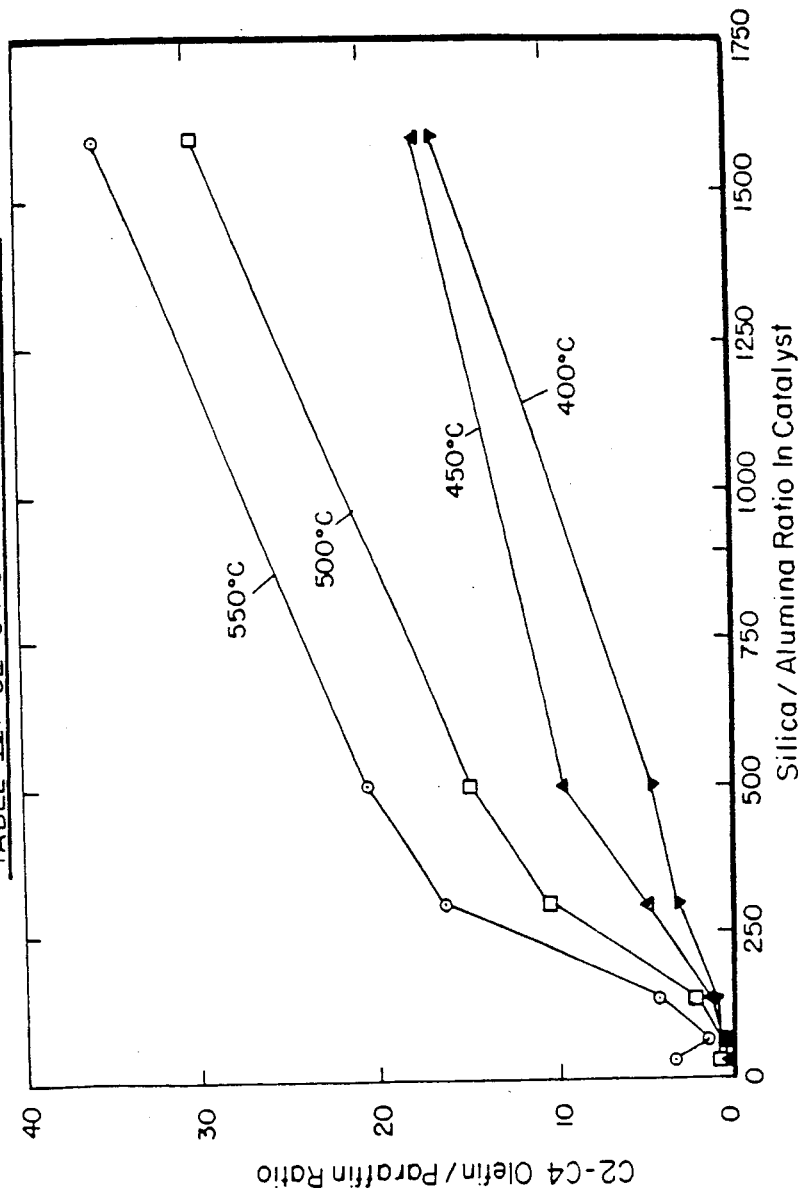

Any composition comprising at least 10 wt.% of alcohol may be used as the alcohol feed in this invention. Methanol is preferred and may be substantially pure, industrial grade anhydrous methanol or even crude methanol containing usually 12 to 20 wt.% of water. Small amounts of impurities such as higher alcohols, aldehydes, or other oxygenated compounds in the alcohol feed have little effect on the conversion process of this invention. The alcohol feed may contain ether compounds, for instance dimethyl ether, since an equilibrium between alcohol and its dialkyl ether and water is rapidly established over catalysts of the type used.

Diluents may be included in the alcohol feed and it is ordinarily preferred that such diluents be substantially anhydrous, although hydrous diluents such as steam may find utility under some process conditions. Preferred anhydrous diluents include, but are not limited to: hydrogen, helium, nitrogen, carbon dioxide, methane, ethane, propane, butanes, pentanes, hexanes, heptanes and flue gas.

The catalyst composition useful in this invention consists essentially of a crystalline aluminosilicate zeolite characterized by a silica to alumina mole ratio of at least 140 and a "constraint index" of from about 1 to about 12, said constraint index being fully defined hereinbelow. Although silica to alumina mole ratios of at least 140 are silica to alumina ratios in excess of 298. Zeolitic catalysts having silica/alumina ratios in the range of 298 to 2000 are particularly preferred.

The zeolite catalysts utilized herein are members of a novel class of zeolites exhibiting some unusual properties. The zeolites induce profound transformation of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. This is especially surprising in the present instance since high activity was observed even with a silica/alumina ratio of 1600/1. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by controlled burning at higher than usual termperatures to restore activity. In many environments the zeolites of this class exhibit very low coke forming capability, conducive to very long times on stream between burning regenerations.

An important characteristic of the crystal structure of this class of zeolites is that it provides constrained access to and egress from the intracrystalline free space by virtue of having a pore dimension greater than about 5 Angstroms and pore windows of about a size such as would be provided by 10-membered rings of silicon and aluminum atoms connected by oxygen. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 140 and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. As mentioned above, although zeolites with a silica to alumina ratio of at least 140 are useful, it is preferred to use zeolites having higher ratios of at least about 298. Such zeolites, after activation, acquire an intracrystalline sorption capacity for normal hexane which is greater than that for water, i.e. they exhibit "hydrophobic" properties. It is believed that this hydrophobic character is advantageous in the present invention.

The zeolites useful in this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective. Twelve-membered rings usually do not offer sufficient constraint to produce the advantageous conversions, although the puckered 12-ring structure of TMA offretite shows constrained access. Other 12-ring structures may exist which, due to pore blockage or to other cause, may be operative.

Rather than attempt to judge from crystal structure whether or not a zeolite possesses the necessary constrained access to molecules larger than normal paraffins, a simple determination of the "Constraint Index" as herein defined may be made by passing continuously a mixture of an equal weight of normal hexane and 3-methylpentane over a small sample, approximately one gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature adjusted between 290° C. and 510° C. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromotography, to determine the fraction remaining unchanged for each of the two hydrocarbons.

The "Constraint Index" is calculated as follows:

$$\text{Constraint Index} = \frac{\log_{10}(\text{fraction of n-hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical zeolites are:

| CAS | C.I. |
| --- | --- |
| ZSM-5 | 8.3 |
| ZSM-11 | 8.7 |
| ZSM-12 | 2 |
| ZSM-35 | 4.5 |
| ZSM-38 | 2 |
| TMA Offretite | 3.7 |
| Beta | 0.6 |
| ZSM-4 | 0.5 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby have different Constraint Indices. Constraint Index seems to vary somewhat with severity of operation (conversion) and the presence or absence of binders. Therefore, it will be appreciated that it may be possible to so select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the novel class of highly siliceous zeolites are those zeolites which, when tested under two or more sets of conditions within the above specified ranges of temperature and conversion, produce a value of the Constraint Index slightly less than 1, e.g. 0.9, or somewhat greater than 12, e.g. 14 or 15, with at least one other value of 1 to 12. Thus, it should be understood that the Constraint Index value as used herein is an inclusive rather than an exclusive value. That is, a zeolite when tested by any combination of conditions within the testing definition set forth hereinabove to have a Constraint Index of 1 to 12 is intended to be included in the instant catalyst definition regardless that the same identical zeolite tested under other defined conditions may give a Constraint Index value outside of 1 to 12.

The class of zeolites defined herein is exemplified by ZSM-5, ZSM-11, ZSM-12, ZSM-35, ZSM-38, and other similar materials. U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-35 is more particularly described in U.S. Pat. No. 4,016,245, the entire content of which is incorporated herein by reference.

ZSM-38 is more particularly described in U.S. Pat. No. 4,046,859, the entire content of which is incorporated herein by reference.

The specific zeolites described, when prepared in the presence of organic cations, are substantially catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite The preferred crystalline aluminosilicates are ZSM-5, ZSM-11, ZSM-12, ZSM-35, and ZSM-38, with ZSM-5 being particularly preferred.

In a preferred aspect of this invention, the zeolites hereof are selected as those having a crystal framework density, in the dry hydrogen form, of not less than about 1.6 grams per cubic centimeter. It has been found that zeolites which satisfy all three of these criteria are most desired for several reasons. When hydrocarbon products or by-products are catalytically formed, for example, such zeolites tend to maximize the production of gasoline boiling range hydrocarbon products. Therefore, the preferred zeolites of this invention are those having a Constraint Index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space. It is possible that the unusual sustained activity and stability of this class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites including some which are not within the purview of this invention are:

| Zeolite | Void Volume | | Framework Density |
|---|---|---|---|
| Ferrierite | 0.28 cc/cc | | 1.76 g/cc |
| Mordenite | .28 | | 1.7 |
| ZSM-5, -11 | .29 | | 1.79 |
| Dachiardite | .32 | | 1.72 |
| L | .32 | | 1.61 |
| Clinoptilolite | .34 | 1.71 | |
| Laumontite | .34 | 1.77 | |
| ZSM-4 (Omega) | .38 | | 1.65 |
| Heulandite | .39 | | 1.69 |
| P | .41 | | 1.57 |
| Offretite | .40 | | 1.55 |
| Levynite | .40 | | 1.54 |
| Erionite | .35 | | 1.51 |
| Gmelinite | .44 | | 1.46 |
| Chabazite | .47 | | 1.45 |
| A | .5 | | 1.3 |
| Y | .48 | | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modifications.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix on an anhydrous basis may vary widely with the zeolite content ranging from between about 1 to about 99 percent by weight and more usually in the range of about 5 to about 80 percent by weight of the dry composite.

The zeolites employed herein may also be physically mixed or diluted with particle-form solid of either an appropriate catalytic nature or substantially devoid of catalytic activity. Typical of the latter are silica particles such as low surface area quartz chips.

The conversion process described herin may be carried out as a batch type, semi-continuous or continuous operation utilizing a fixed or moving bed catalyst system. The catalyst after use in a moving bed reactor is conducted to a regeneration zone wherein coke is burned from the catalyst in an oxygen-containing atmosphere, e.g. air, at an elevated temperature, after which the regeneraged catalyst is recycled to the conversion zone for further contact with the charge stock. In a fixed bed reactor, regeneration is carried out in a conventional manner where an inert gas containing a small amount of oxygen (0.5-2%) is used to burn the coke in a controlled manner so as to limit the temperature to a maximum of around 500°-550° C.

As discussed above, the preferred alcohol feed is methanol. Subsequent discussion of the conversion process of this invention will be with reference to a methanol feed stock, but it is to be understood that such reference is intended to be for purposes of elucidating the invention and should not be taken as limiting in any manner on the novel process disclosed herein.

The methanol feed is passed over the catalyst at a rate of 0.5 to 10 WHSV (weight hourly space velocity), preferably at 1 to 5 WHSV. In all cases, the WHSV is calculated on the pounds of methanol feed per hour per pound of catalyst. For the purposes of this invention, the methanol feed and optional diluent are contacted with the catalyst at a pressure of 1 to 100 atmospheres, (i.e. at a pressure of 760 to 76,000 mm Hg.) It is preferred, however, to conduct the reaction at from 1 to about 10 atmospheres. The conversion is carried out at temperatures between about 350° C. and 600° C., with the preferred operating temperature range being between about 400° C. and 550° C. The temperatures referred to herein are to be understood to refer to the maximum temperature within the reaction zone. Thus, in a fixed-bed operation, the inlet temperature may be lower than 350° C. Within the prescribed conditions, a conversion per pass of from 50% to about 100% of the methanol may be achieved and the ratio of $C_2$-$C_4$ olefins to paraffins in the product mix is significantly enhanced.

The term "conversion", as used herein, is to be understood to mean a chemical change in which a hydrocarbon having at least two carbon atoms is formed. Thus, a substantially pure methanol feed will form an equilibrium mixture of alcohol, ether and water initially which is then further converted to a mixture of hydrocarbons and water. This dimethyl ether is ignored in computing conversion since no new carbon-carbon bonds are created in its formation. If some dimethyl ether is present in the methanol feed, its conversion to hydrocarbons is added to that of the methanol to arrive at the "conversion" value. Specifically, 80% conversion as used herein means that 80% of the total —$CH_2$— groups present in the methanol and dimethyl ether of the methanol feed are converted to hydrocarbons.

After the catalyst has been on stream for sufficient time to accumulate inactivating deposits and is no longer effective, its activity may be restored by contact with oxygen-containing gas at sufficiently elevated temperature to burn away the deposits.

The hydrocarbon mixture produced by the process of this invention is recovered and the olefins concentrated and separated by distillation or other techniques well understood in the art.

The following examples will serve to illustrate the process of the invention without limiting the same:

Example 1

ZSM-5 characterized by a high silica/alumina mole ratio (~1600/1) was prepared as follows:

I-Prereacted Organics Preparation

The following materials were charged to a 30 gallon autoclave: 16,524 grams of methylethyl ketone, 10,008 grams of tri-n-propylamine and 8604 grams of n-propyl bromide. The contents were mixed with gentle agitation for 15 minutes. The agitation was stopped and 55.8 kg of water were charged to the autoclave. The autoclave was sealed and heated to 104° C. and held at 104° C. for 15 hours. After this reaction period, the temperature was raised to 160° C. and the unreacted organics were flashed off. The aqueous phase was removed containing the prereacted organics and contained 1.44 wt% nitrogen.

II - Zeolite Synthesis (a) Solution Preparation

Silicate Solution
41.23 kg Q-brand sodium silicate
23.86 kg $H_2O$
118 g Daxad 27 (sodium salt of polymerized substituted benzenoid alkyl sulfonic acid combined with a suspending agent)

Acid Solution
4138 g. $H_2SO_4$
1840 g. NaCl
50.7 g. Prereacted organics
6.67 kg $H_2O$ Additional Solids
5890 g. NaCl Additional Liquid
1180 g. $H_2O$ (b) Procedure The silicate solution and acid solution were mixed in a mixing nozzle to form a gel which was discharged into a 30 gallon autoclave to which 1180 grams of water had been previously added. The gel was whipped by agitation and 5890 grams of NaCl were added and thoroughly blended. The autoclave was sealed and heated to ~104° C. with agitation at 90 rpm and held for 54.3 hours until crystallization was completed. The contents of the autoclave were cooled and discharged. The crystallized product was analyzed by X-ray diffraction and was found to be 100 wt.% ZSM-5. The chemical analysis of the thoroughly washed crystalline product was:

|  | As Received | Fired Basis | Mole Ratio |
|---|---|---|---|
| $Al_2O_3$, % wt. | 0.09 | 0.10 | 1.0 |
| $SiO_2$, % wt. | 84.1 | 98.3 | 1670 |
| Na, % wt. | 1.4 | 1.6 | — |
| N, % wt. | 0.75 | — | 35.5 |
| C, % wt. | 8.98 | — | 63.9 |
| $H_2O$ and other volatiles | 4.68 | — | 892 |
|  | 100.00 | 100.00 |  |

Example 2

ZSM-5 having a silica/alumina mole ratio of about 70 was prepared as follows:

850 kg of tri-n-propylamine were mixed with 730.3 kilograms of n-propyl bromide, 1406 kg of methyl ethyl ketone and 4747 liters of deionized water. The mixture was reacted at 99°–103° C., 5 rpm for 14 hours in an autoclave equipped with high shear agitation. The resulting aqueous phase was designated solution A.

2218 liters of deionized water were mixed with enough Q-brand sodium silicate to give a solution with a specific gravity of 1.222. 10.9 kilograms of Daxad 27 were added to the solution. The resulting solution was designated Solution B.

138.3 kilograms of commercial grade aluminum sulfate (17.2% $Al_2O_3$) were dissolved in 1654 liters of deionized water. To this solution, 332.5 kg of sulfuric acid (93.2 wt.% $H_2SO_4$), 171.0 kg of commercial grade NaCl and 868.6 kg of Solution A were added. The resulting solution was designated Solution C.

75 liters of deionized water were added to an autoclave equipped with high shear agitation. Solution B and Solution C were mixed simultaneously in a nozzle and sprayed into the autoclave. 544.3 kilograms of commercial grade NaCl were added to the autoclave. The resulting gel was mixed in the autoclave at 90 rpm and ambient temperature for 4 hours. The gel was then reacted at 97°–108° C. and 90 rpm for 40 hours and at 160° C. and 90 rpm for 3 hours. The solid product was analyzed by X-ray diffraction and found to be ZSM-5. The solid product was washed by decantation with deionized water and 3500 ppm Primafloc C-7 (polyammonium bisulfate) until the sodium content of the product was less than 1%. The solid product was filtered on a rotary drum filter. The resulting filter cake was dried at 154° C.

The chemical analysis of the dried product was:

|  | As Received | Fired Basis | Mole Ratio |
|---|---|---|---|
| $Al_2O_3$, % wt. | 2.09 | 2.39 | 1.0 |
| $SiO_2$, % wt. | 84.8 | 97.0 | 68.9 |
| Na, % wt. | 0.84 | 0.96 | — |
| N, % wt. | 0.85 | — | .89 |
| C, % wt. | 7.98 | — | 2.59 |
| $H_2O$ and other volatiles | 3.44 | — | 28.4 |
|  | 100.00 | 100.35 |  |

1.4–1.8 kilograms of the dried product were calcined in $N_2$ for 3 hours at 538° C.

1329 grams of the calcined product were mixed with 6645 cc of 1N $NH_4NO_3$ solution for 1 hour at ambient temperature. The mixture was vacuum filtered. The ion exchange procedure was repeated and the final filter cake was dried at 121° C. The sodium content of the final product was less than 0.05 wt.%.

Other ratios of $SiO_2/Al_2O_3$ in HZSM-5 catalysts may be obtained by appropriately adjusting the amounts of silicon and aluminum reagents used in the catalyst synthesis procedure.

Examples 3–6 (Normal silica/alumina ratio in catalyst)

Methanol was converted to hydrocarbon products in an electrically heated, tubular, fixed fed, quartz reactor which contained a thermowell in the center of the catalyst bed to measure temperature. Liquid feed was pumped at the desired rate to a preheater to vaporize it and bring it to the desired temperature. The reaction products were condensed in a water cooled receiver followed by a dry ice trap. The gases which were not condensed were collected in a calibrated tower by displacement of water. All products were analyzed by standard gas chromatography techniques and the data calculated by means of a computer.

Five grams (9.6 ml) of the catalyst, prepared by the method in Example 2 above (with a $SiO_2/Al_2O_3$ ratio of 70/1) were pressed into wafers, crushed and sized to 14-20 mesh, diluted uniformly with about 4 volumes of 14-20 mesh, low surface area quartz chips and centered in the catalytic reactor. Methanol at a weight hourly space velocity (WHSV) of 4.0 at atmospheric pressure was passed through the catalyst bed at 4 different temperatures. The conversion of methanol to hydrocarbons and water was very high (97-100%). The selectivity to the various hydrocarbon products is summarized in Table II. It can be seen that roughly half of the products were $C_2$-$C_4$ aliphatics and that paraffins dominated olefins produced for all but the run at the highest temperature.

were, except at the highest temperature, significantly larger than the corresponding olefins.

Examples 7-10 (High silica/alumina ratio in catalyst)

Using the same procedure as above, five grams of the catalyst of Example 1 (with a $SiO_2/Al_2O_3$ ratio of 1600/1) were diluted with 4 volumes of low surface area quartz. The conditions of reaction duplicated those of Examples 3-6 and only the temperature was varied from run to run. The results are summarized in Table III.

TABLE III

| | $SiO_2/Al_2O_3$ ratio = 1600/1 | | | | | | | |
|---|---|---|---|---|---|---|---|---|
| | Example No. | | | | | | | |
| | 7 | | 8 | | 9 | | 10 | |
| Temp. °C. | 400 | | 450 | | 500 | | 550 | |
| Conversion, wt. % | 27.6 | | 99.7 | | 100.0 | | 100.0 | |
| Selectivity To Products, wt. % | | | | | | | | |
| CO + $CO_2$ | 3.6 | | 1.2 | | 4.2 | | 7.7 | |
| $CH_4$ | 3.7 | | 2.0 | | 5.7 | | 10.6 | |
| $C_2H_6$ | 0.04 | | 0.1 | | 0.4 | | 0.8 | |
| $C_2H_4$ | | 6.6 | | 5.2 | | 8.5 | | 12.2 |
| $C_3H_8$ | 0.5 | | 0.7 | | 0.5 | | 0.4 | |
| $C_3H_6$ | | 28.6 | | 32.1 | | 33.1 | | 30.4 |
| $C_4H_{10}$ | 2.8 | | 2.6 | | 1.1 | | 0.3 | |
| $C_4H_8$ | | 18.0 | | 22.0 | | 17.7 | | 10.4 |
| (SUBTOTAL) | (3.3) | (53.5) | (3.4) | (59.3) | (2.0) | (59.3) | (1.5) | (53.0) |
| $C_5$ | 11.4 | | 12.1 | | 9.5 | | 4.3 | |
| $C_6$ | 5.3 | | 6.5 | | 4.3 | | 1.6 | |
| $C_7$ | 10.3 | | 6.6 | | 2.5 | | 1.1 | |
| Benzene | 0.5 | | 0.7 | | 0.8 | | 0.9 | |
| Toluene | 1.2 | | 0.8 | | 1.1 | | 2.7 | |
| Xylene | 2.1 | | 2.2 | | 3.4 | | 6.5 | |
| $C_9$+ | 5.1 | | 5.2 | | 7.2 | | 10.1 | |
| Total | 100.0 | | 100.0 | | 100.0 | | 100.0 | |

It is evident that a dramatic change in composition of the $C_2$-$C_4$ products has occurred. The selectivities to $C_2$-$C_4$ olefins increased to greater than 50 percent of the total hydrocarbon products and the olefin/paraffin ratios were likewise increased to as high as 35/1.

TABLE II

| | $SiO_2/Al_2O_3$ ratio = 70/1 | | | | | | | |
|---|---|---|---|---|---|---|---|---|
| | Example No. | | | | | | | |
| | 3 | | 4 | | 5 | | 6 | |
| Temp. °C. | 400 | | 450 | | 500 | | 550 | |
| Conversion, wt. % | 100 | | 100 | | 100 | | 100 | |
| Selectivity to Products, wt. % | | | | | | | | |
| CO + $CO_2$ | 0.2 | | 0.8 | | 1.8 | | 1.6 | |
| $CH_4$ | 0.5 | | 1.8 | | 2.3 | | 5.6 | |
| $C_2H_6$ | 0.2 | | 0.9 | | 1.2 | | 1.5 | |
| $C_2H_4$ | | 3.4 | | 6.4 | | 6.8 | | 15.6 |
| $C_3H_8$ | 6.9 | | 11.4 | | 14.9 | | 10.3 | |
| $C_3H_6$ | | 3.9 | | 6.4 | | 7.3 | | 14.4 |
| $C_4H_{10}$ | 20.1 | | 19.8 | | 19.3 | | 13.0 | |
| $C_4H_8$ | | 9.6 | | 7.4 | | 6.4 | | 8.0 |
| (SUBTOTAL) | (27.2) | (16.9) | (32.1) | (20.0) | (35.4) | (20.5) | (24.8) | (32.8) |
| $C_5$ | 8.5 | | 4.8 | | 2.8 | | 2.1 | |
| $C_6$ | 8.6 | | 4.0 | | 1.8 | | 1.1 | |
| $C_7$ | 5.5 | | 1.3 | | 0.4 | | 0.2 | |
| Benzene | 0.5 | | 1.2 | | 1.7 | | 1.2 | |
| Toluene | 3.5 | | 7.1 | | 8.6 | | 6.0 | |
| Xylene | 11.3 | | 13.8 | | 14.2 | | 11.1 | |
| $C_9$+ | 17.3 | | 12.9 | | 10.5 | | 8.9 | |
| Total | 100.0 | | 100.0 | | 100.0 | | 100.0 | |

As shown by the data, the amounts of $C_2$-$C_4$ paraffins produced using the 70/1 $SiO_2/Al_2O_3$ zeolite catalyst Examples 11-16

To further demonstrate the significance of the present invention, a number of zeolitic catalysts with silica/alumina ratios varying from 1600/1 to 35/1 were tested for their ability to convert methanol to hydrocarbons in the 400°–550° C. range at atmospheric pressure and a WHSV of approximately 4. The results are summarized in Table IV, which shows the $C_2$–$C_4$ ratios of olefins/paraffins produced.

TABLE IV

| Example No. | $SiO_2$/ $Al_2O_3$ | Conversion, wt. % | $C_2$–$C_4$ olefin/paraffin ratio | | | |
|---|---|---|---|---|---|---|
| | | | 400° C. | 450° C. | 500° C. | 550° C. |
| 11 | 1600/1 | 100* | 16.2 | 17.4 | 29.7 | 35.3 |
| 12 | 500/1 | 100 | 4.4 | 9.6 | 14.8 | 20.6 |
| 13 | 298/1 | 100 | 2.9 | 4.9 | 10.5 | 16.4 |
| 14 | 140/1 | 100 | 0.8 | 1.2 | 2.1 | 4.3 |
| 15 | 70/1 | 100 | 0.6 | 0.6 | 0.6 | 1.5 |
| 16 | 35/1 | 100 | 0.3 | 0.3 | 0.9 | 3.4 |

NOTE:
*Except at 400° C., where the conversion was 36.6%.

FIG. I is a graphical representation of the data of Table IV. As can be seen from the graph, when the $SiO_2/Al_2O_3$ ratio is above about 140 the ratio of olefins to paraffins changes significantly to favor the olefins at essentially 100 percent conversion of the methanol. 34 35 36 37 38 39 40 41 42 43 44 45 46 47

TABLE V

| Example No. | $SiO_2/Al_2O_3$ | Selectivity, wt. %, to $C_2$–$C_4$ olefin | | | |
|---|---|---|---|---|---|
| | | 400° C. | 450° C. | 500° C. | 550° C. |
| 11 | 1600/1 | 53.5 | 59.3 | 59.3 | 53.0 |
| 12 | 500/1 | 34.2 | 53.9 | 68.1 | 70.1 |
| 13 | 298/1 | 36.2 | 53.9 | 69.0 | 70.1 |
| 14 | 140/1 | 19.9 | 30.5 | 39.7 | 51.2 |
| 15 | 70/1 | 16.9 | 20.2 | 20.5 | 38.0 |
| 16 | 35/1 | 11.3 | 10.2 | 23.3 | 35.4 |

It can be seen that olefin selectivity increases directly and dramatically with both increases in temperature and in the silica/alumina ratio of the catalyst.

It is to be understood that the foregoing description, with reference to specific embodiments and examples employing methanol feed stock and specific operating parameters, has been for the purpose of demonstrating the invention and should not be considered as limiting in any manner on the novel process of my discovery. As will be readily apparent to those skilled in the art, optimization of process conditions and utilization of feedstocks other than methanol would not alter the principle disclosed herein and, indeed, would be expected by those in the art practicing my invention. Such changes and modifications are intended to fall within the purview and scope of the appended claims.

What is claimed is:

1. In a method for producing a hydrocarbon mixture by catalytic conversion of an alcohol feed over a crystalline aluminosilicate zeolite catalyst, the improvement, whereby the proportion of olefins in said hydrocarbon mixture is increased, which comprises contacting said alcohol feed under sufficient alcohol conversion conditions including a reaction temperature of from 350° C. to 600° C., a WHSV of alcohol of 0.5 to 10, and a reaction pressure of from 1 to 100 atmospheres, with a crystalline aluminosilicate zeolite catalyst characterized by having a constraint index within the approximate range of 1 to 12 and a silica to alumina ratio of from 298 to 2000.

2. The improved process of claim 1 wherein said olefins whose proportion in said hydrocarbon mixture is increased comprise olefinic hydrocarbons having approximately two to four carbon atoms per molecule.

3. The improved process of claim 1 wherein said crystalline aluminosilicate zeolite is admixed with a solid diluent or with a binder therefor.

4. In a method for producing a hydrocarbon mixture by catalytic conversion of an alcohol feed over a crystalline aluminosilicate zeolite catalyst, the improvement, whereby the proportion of olefins in said hydrocarbon mixture is increased, which comprises contacting said alcohol feed under sufficient alcohol conversion conditions including a reaction temperature of 350° C. to 600° C., a WHSV of alcohol of from 0.5 to 10, a reaction pressure of from 1 to 100 atmospheres, and the absence of a diluent in the alcohol feed, with a crystalline aluminosilicate zeolite catalyst characterized by having a constraint index within the approximate range of 1 to 12 and a silica to alumina ratio of from 298 to 2000.

5. The improved process of claim 4 wherein said olefins whose proportion in said hydrocarbon mixture is increased comprise olefinic hydrocarbons having approximately two to four carbon atoms per molecule.

6. The improved process of claim 4 wherein said crystalline aluminosilicate zeolite is admixed with a solid diluent or with a binder therefor.

7. In a method for producing a hydrocarbon mixture by catalytic conversion of a methanol feed over a crystalline aluminosilicate zeolite catalyst, the improvement, whereby the proportion of olefins in said hydrocarbon mixture is increased, which comprises contacting said methanol feed under methanol conversion conditions including a reaction temperature of from about 400° C. to 550° C., a WHSV of methanol of from 1 to 5, a reaction pressure of from 1 to 10 atmospheres, and the absence of a diluent in the methanol feed, with a ZSM-5 crystalline aluminosilicate zeolite catalyst having a silica to alumina ratio of from 298 to 2000.

8. The improved process of claim 7 wherein said olefins whose proportion in said hydrocarbon mixture is increased comprise olefinic hydrocarbons having approximately two to four carbon atoms per molecule.

9. The improved process of claim 7 wherein said crystalline aluminosilicate zeolite is admixed with a solid diluent or with a binder therefor.

10. Th improved process of claim 1 wherein said alcohol is methanol.

11. The improved process of claim 10 wherein the conversion of said methanol is from 50% to 100%.

12. The improved process of claim 11 wherein said conversion of methanol is at least 80%.

13. The improved process of claim 10 wherein the conversion of said methanol is from 97% to 100%.

14. The improved process of claim 13 wherein said conversion of methanol is 100%.

15. The improved process of claim 7 wherein the conversion of said methanol is from 50% to 100%.

16. The improved process of claim 15 wherein said conversion of methanol is at least 80%.

17. The improved process of claim 7 wherein the conversion of said methanol is from 97% to 100%.

18. The improved process of claim 17 wherein said conversion of methanol is 100%.

19. The improved process of claim 9 wherein said conversion of methanol is at least 80%.

* * * * *

UNITED STATES PATENT AND TRADEMARK OFFICE
CERTIFICATE OF CORRECTION

PATENT NO. : 4,849,573

DATED : July 18, 1989

INVENTOR(S) : Warren W. Kaeding

It is certified that error appears in the above-identified patent and that said Letters Patent is hereby corrected as shown below:

Col. 3, line 30, after "are" insert --useful in the present invention, the preferred catalyst will have--
Col. 7, line 9, "1.71" should be under column 3.
Col. 7, line 10, "1.77" should be under column 3.
Col. 13, line 24, delete "34 35 36 37 38 39 40 41 42 43 44 45 46 47".
Col. 13, line 25, insert as a new paragraph before the Table V chart, --In Table V, which has been graphically reproduced in Figure II of the drawings, the selectivity to $C_2$-$C_4$ olefins is shown for Examples 11-16.--
Col. 14, Claim 10, line 1, "Th" should be --The--.

Signed and Sealed this

Nineteenth Day of June, 1990

Attest:

HARRY F. MANBECK, JR.

*Attesting Officer*  *Commissioner of Patents and Trademarks*